United States Patent [19]

Cassou

[11] 4,261,361

[45] Apr. 14, 1981

[54] INJECTING SYRINGE IN PARTICULAR FOR THE ARTIFICIAL INSEMINATION OF DOMESTIC ANIMALS

[76] Inventor: Bertrand Cassou, Saint Symphorien des Bruyeres, 61300 L'Aigle, France

[21] Appl. No.: 89,861

[22] Filed: Oct. 31, 1979

[51] Int. Cl.$^3$ .............................................. A61M 1/00

[52] U.S. Cl. .................................................... 128/235

[58] Field of Search ............... 128/235, 234, 220, 221, 128/224, 237

[56] References Cited

U.S. PATENT DOCUMENTS 4,173,227 11/1979 Cassou et al. ........................ 128/235

FOREIGN PATENT DOCUMENTS 1224918 6/1960 France .................................... 128/235

1467943 2/1967 France .................................... 128/235

1525336 5/1968 France .................................... 128/235

2358136 10/1978 France .................................... 128/235

*Primary Examiner*—John D. Yasko

*Attorney, Agent, or Firm*—Kenyon & Kenyon

[57] ABSTRACT

The syringe is of the type comprising a tubular body 1 adapted to receive a supply of product to be injected and in which is slidably mounted a push-rod for expelling the product from the supply, and a flexible sheath 3 which surrounds the tubular body and is detachably fixed around a holding end 4 of the body. The holding end 4 of the tubular body has projections 6 whose height, measured from the axis of the body exceeds the inside diameter of the fixing end of the sheath 3.

5 Claims, 2 Drawing Figures

Figure 2:
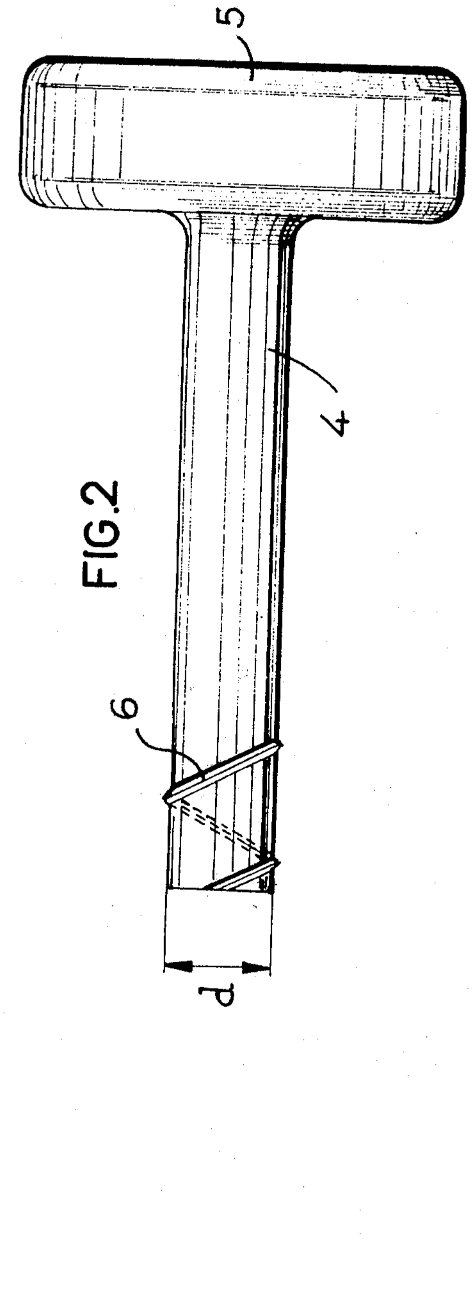

INJECTING SYRINGE IN PARTICULAR FOR THE ARTIFICIAL INSEMINATION OF DOMESTIC ANIMALS

The present invention relates to injecting syringes, in particular for the artificial insemination of domestic animals, of the type comprising, on one hand, a tubular body which is adapted to receive a supply of product to be injected and in which is slidably mounted a push-rod adapted to expel this product from the supply, and, on the other hand, a flexible sheath which surrounds this tubular body and is detachably fixed around a holding end of the body. The purpose of the sheath is to avoid any contact of the syringe body with the animal and consequently any contamination and the body of the syringe can remain sterile in the course of multiple injection operations in respect of each of which operations the protecting sheath is however changed.

Syringes of this type are known, for example from French Pat. Nos. 1 224 918, 1 467 943, 1 525 336 and 2 358 136, in which the detachable fixing of the sheath to the syringe body is achieved by means of a ring which forcefully clamps the end of the sheath on a frustoconical surface of the body specially provided for this purpose.

However, such an arrangement has the drawback of giving the holding end of the body a diameter which is distinctly larger than its normal diameter which considerably hinders the vision of the user, in particular in the case of the insemination of sheep in respect of which the vagina dimensions are very small and moreover the work is carried out between the rather closely spaced end sides of a speculum. Another drawback resides in the considerable risk of loss of the ring and an imperfect use of the syringe.

Consequently, an object of the present invention is to overcome these drawbacks and for this purpose it provides a syringe of the aforementioned type wherein the holding end of the tubular body provides projections whose height, measured from the axis of this body, exceeds the inside diameter of the fixing ends of the sheath.

In a particularly advantageous embodiment of the invention, it may be arranged that said projections be formed by a surface which extends along a helical profile around the holding end of the tubular body and projects from the diameter of the body part of this end. Preferably, the projecting helical surface extends through at least one turn of the helix and the helical projection has a triangular radial sectional shape.

Also advantageously, in the case where the holding end of the tubular body is formed by an attached member which is also tubular and is mounted on and fixed to the body, the outside diameter of the body part of this member above which said projections are provided may be approximately equal to the inside diameter of the sheath.

Owing to this arrangement, when the operator presents his sheath, he easily engages it on the projections of the tubular body which are inserted in the inner wall of the sheath. In the case of a helical projection, the operator turns the sheath through a few turns on the body in order to achieve a satisfactory anchoring. Thus, the outside diameter of the holding end of the body has been reduced as far as possible and this improves visibility when injecting. Further, this fixing of the sheath is very reliable, rapid and progressive. Thus, the risk of loss of a ring is avoided.

Figure 1:
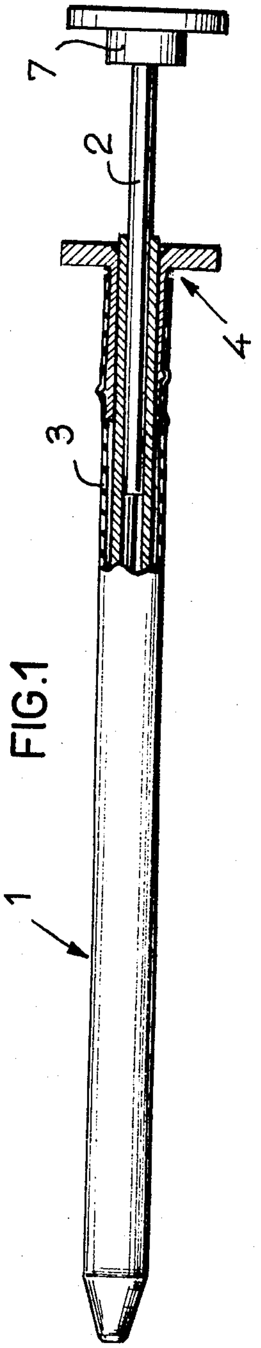

Further features and advantages of the invention will be apparent from the ensuing description which is given merely by way of example with reference to the accompanying drawings in which:

FIG. 1 is a partial sectional view of a syringe according to one embodiment of the invention, and FIG. 2 is a view to an enlarged scale of the holding end or head of this syringe.

The illustrated syringe comprises, on one hand, a tubular body 1 which is adapted to receive a supply of product to be injected and in which is slidably mounted a push-rod 2 for expelling the product from the supply, and, on the other hand, a not split flexible sheath 3 which surrounds this tubular body 1 and is detachably fixed around a holding end 4 of the latter. This holding end 4 is formed by an attached member which is also tubular but of shorter length than the body and is mounted on and fixed to the end of this body which received the push-rod 2. This member has an approximately constant wall thickness throughout its length except for one end adjacent to the push-rod where it terminates in a holding head 5 of annular shape.

At the end opposed to the head 5, the attached member 4 has projections formed by a surface 6 which extends along a helical profile around the member 4 and projects from the outside diameter d of the body part of this member. This helical surface extends, for example, through one and a half turns of the helix and its radial section is in the shape of an equilateral triangle.

The outside diameter of the body part d of the member 4 is approximately equal to the inside diameter of the sheath 3 so that, when the latter is mounted on the tubular body and the attached member 4, this sheath is forcefully applied on top of the coil 6 which penetrates the inner wall of the sheath.

Thus, the outside diameter of the attached member 4, or the holding end of the tubular body, is reduced to a minimum since it remains constant on the major part of its length, whereas the diameter of the head 5 may also be reduced to a value which exceeds no more than one half of the body part of the member 4. Further, the diameter of the actuating head 7 of the push-rod 2 is also reduced to a minimum to the same extent as the head 5.

In addition to this advantage improving the visibility for the observer, are the facility and effectiveness of the fixing of the sheath, the elimination of the risk of loss of a ring, the elimination of the risk of contamination by the use of the same ring for several successive operations, and, finally, the possibility of achieving a more precise injection which is less awkward for operators who have small fingers since they gain 15 mm by the elimination of the ring.

I claim:

1. Injecting syringe in particular for artificial insemination of domestic animals, comprising a tubular body having a holding end portion and adapted to receive a supply of product to be injected, a push-rod slidably mounted in the body for expelling said product from the supply and a flexible sheath which surrounds the tubular body and has a fixing end portion, said holding end portion of the tubular body comprising projections which have a height measured from the axis of the body, which exceeds the one half of the inside diameter of the fixing end portion of the sheath and thereby fix the sheath to the holding end portion.

2. A syringe as claimed in claim 1, wherein said projections are formed by a surface which extends along a helical profile around the holding end portion of the tubular body and projects from the diameter of a body part said holding end portion.

3. A syringe as claimed in claim 2, wherein the projecting helical surface extends through at least one turn of the helix.

4. A syringe as claimed in claim 2 or 3, wherein the helical projection has a triangular radial sectional shape.

5. A syringe as claimed in any one of the claims 1 to 4, wherein the holding end portion of the tubular body is constituted by an attached tubular member which is mounted and fixed on the body, and the outside diameter of a body part of said attached member about which body part said projections are provided is substantially equal to the inside diameter of the sheath.

* * * * *